(12) United States Patent
Yam et al.

(10) Patent No.: US 9,691,989 B2
(45) Date of Patent: Jun. 27, 2017

(54) CARBO- AND HETEROCYCLIC SPIRO COMPOUNDS AS DONOR MATERIALS FOR ORGANIC PHOTOVOLTAICS AND THEIR PREPARATION

(71) Applicant: The University of Hong Kong, Hong Kong (CN)

(72) Inventors: Vivian Wing-Wah Yam, Hong Kong (CN); Chin-Yiu Chan, Hong Kong (CN); Mei-Yee Chan, Hong Kong (CN)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 0 days.

(21) Appl. No.: 14/823,520

(22) Filed: Aug. 11, 2015

(65) Prior Publication Data

US 2016/0043323 A1    Feb. 11, 2016

Related U.S. Application Data

(60) Provisional application No. 62/035,602, filed on Aug. 11, 2014.

(51) Int. Cl.
| | |
|---|---|
| C07D 335/12 | (2006.01) |
| H01L 51/00 | (2006.01) |
| C07D 311/96 | (2006.01) |
| C07D 221/20 | (2006.01) |
| C07C 211/54 | (2006.01) |
| C07D 335/04 | (2006.01) |
| C07D 409/14 | (2006.01) |
| C07D 209/86 | (2006.01) |
| C07D 333/78 | (2006.01) |
| H01L 51/42 | (2006.01) |

(52) U.S. Cl.
CPC ........ *H01L 51/0056* (2013.01); *C07C 211/54* (2013.01); *C07D 209/86* (2013.01); *C07D 221/20* (2013.01); *C07D 311/96* (2013.01); *C07D 333/78* (2013.01); *C07D 335/04* (2013.01); *C07D 409/14* (2013.01); *H01L 51/0059* (2013.01); *H01L 51/0072* (2013.01); *H01L 51/0074* (2013.01); *C07C 2103/94* (2013.01); *H01L 51/0046* (2013.01); *H01L 51/0052* (2013.01); *H01L 51/4253* (2013.01); *Y02E 10/549* (2013.01)

(58) Field of Classification Search
USPC ............ 549/26, 27; 548/440, 26, 27, 24, 25; 313/504
See application file for complete search history.

(56) References Cited

U.S. PATENT DOCUMENTS 7,318,966 B2 *   1/2008   Tominaga ............... C07C 15/28
                                                            257/40

* cited by examiner

*Primary Examiner* — Charanjit Aulakh
(74) *Attorney, Agent, or Firm* — Saliwanchik, Lloyd & Eisenschenk

(57) ABSTRACT

The subject invention provides compositions of and methods of using carbo- and heterocyclic spiro compounds as donor materials for organic photovoltaic (OPV) devices. In preferred embodiments, spiro compounds comprising triarylamine and derivatives thereof demonstrate effective hole-transporting properties in OPV devices, achieving up to 5.46% of power conversion efficiency. Advantageously, preferred compounds provided herein are thermally stable and volatile enough to form thin films for the photoactive layer of an OPV device by vacuum deposition or by spin-coating.

4 Claims, 6 Drawing Sheets

CARBO- AND HETEROCYCLIC SPIRO COMPOUNDS AS DONOR MATERIALS FOR ORGANIC PHOTOVOLTAICS AND THEIR PREPARATION

CROSS-REFERENCE TO RELATED APPLICATION

This application claims the benefit of U.S. Provisional Application Ser. No. 62/035,602, filed Aug. 11, 2014, which is hereby incorporated by reference in its entirety, including any figures, tables, or drawings.

BACKGROUND OF THE INVENTION

The present invention is directed to the utilization of carbo- and heterocyclic spiro compounds as donor materials in the fabrication of organic photovoltaic (OPV) devices.

OPV devices have attracted enormous interest over the last two decades because of their great technological potential as a renewable, alternative source for electrical energy. Significant advances on the development of smart materials and innovative device engineering have boosted the power conversion efficiencies (PCE) up to 9.2% for a single cell and up to 10.6% for a tandem device. Up until now, most of the OPV devices with record-high PCEs are based on the use of newly synthesized polymers or oligomers as donor materials in combination with fullerene acceptors (Z. He, C. Zhong, S. Su, M. Xu, H. Wu, Y. Cao, *Nat. Photonics* 2012, 6, 591; J. You, L. Dou, K. Yoshimura, T. Kato, K. Ohya, T. Moriarty, K. Emery, C. Chen, J. Gao, Y. Yang, *Nat. Commun.* 2013, 4, 1446). However, the major challenges for fabricating highly efficient polymeric OPV devices include the difficulty to produce high quality thin films as well as to achieve high batch-to-batch reproducibility. In addition, it is very difficult to control the morphology and phase separation of the blended active layer, which plays a vital role in determining the overall device performance. On the other hand, small molecules are monodispersed in nature with well-defined chemical structure and are synthetically well reproducible with high purity. In comparison to polymer-based thin films, it is also much easier to produce high quality and uniform thin films based on small molecules by vacuum deposition.

While small molecule-based OPV devices can in principle have higher performance and longer stability, the development of small molecule-based OPV devices has received less attention owing to their relatively lower PCEs compared to those of their polymer counterparts. The first small molecule-based bilayer OPV device was demonstrated by Kearns and Calvin in 1958, in which a reasonably high photovoltage of 200 mV with a power output of $3 \times 10^{-12}$ W was obtained for a bilayer magnesium phthalocyanine and oxidized tetramethyl-p-phenylenediamine device (D. Kearns, M. Calvin, *J. Chem. Phys.* 1958, 29, 950). In 1986, Tang reported a highly efficient bilayer OPV device based on copper phthalocyanine (CuPc) as donor and 3,4,9,10-perylenetetracarboxylic bisbenzimidazole (PTCBI), an analogue of perylene bisimide, as acceptor to form a p-n junction. A PCE of approximately 1% with a high fill factor (FF) of 0.65 was recorded under simulated Air Mass (AM) 2 illumination (C. W. Tang, *Appl. Phys. Lett.* 1986, 48, 183). This successful demonstration was believed to be due to the careful choice of photoactive materials. In particular, a large energy offset between the CuPc donor and the PTCBI acceptor at the organic heterojunction provided a sufficiently large driving force for efficient exciton dissociation, yielding a dramatic PCE enhancement as compared to single layer devices.

This breakthrough can be traced back to the discovery of fullerene which exhibits excellent electron-transporting property and can be applied as an acceptor material in OPV devices (N. S. Sariciftci, D. Braun, C. Zhang, V. I. Srdanov, A. J. Heeger, G. Stucky, F. Wudl, *Appl. Phys. Lett.*, 1993, 62, 585). Since then, there have been numerous reports of high efficiency OPV devices utilizing fullerene derivatives as acceptor materials. Fullerene derivatives are the most promising candidates as acceptor materials in OPV devices. However, there still remains a need for the development of good hole-transporting materials as donors in combination with fullerene to result in an efficient OPV device.

Spirobifluorene and its derivatives are among the most well-known classes of hole-transporting materials owing to their high hole-mobilities of up to the order of $10^{-3}$ cm$^2$ V$^{-1}$ s$^{-1}$. The spiro-linkage between two fluorene units with a sp$^3$-hybridized carbon atom can lead to the perpendicular arrangement of two halves, giving structural rigidity. In addition, such three-dimensional (3D) character of spirobifluorene can increase its solubility and glass transition temperature ($T_g$) (T. P. I. Saragi, T. Spehr, A. Siebert, T. F. Lieker, J. Salbeck, *Chem. Rev.* 2007, 107, 1011). The conjugation along the horizontal orientation of the molecules can also increase the intermolecular charge transport property in vacuum-deposited thin films (C. Wu, W. Liu, W. Hung, T. Liu, Y. Lin, H. Lin, K. Wong, Y. Chien, R. Chen, T. Hung, T. Chao, Y. Chen, *Appl. Phys. Lett.* 2005, 87, 052103). Inspired by this structural feature, spirobifluorene and its derivatives have been widely employed as hole-transporting layers in organic light-emitting devices (OLEDs).

Compared with the large number of publications exploring the use of spirobifluorenes as hole-transporting materials in OLEDs, there is less attention on their use in fabricating OPV devices. Indeed, spirobifluorene has a very low absorption coefficient within the visible spectrum and could be harmful to the photovoltaic process. Recently, the possibility of using spirobifluorene as a building block with anchoring groups to construct sensitizers for OPV devices has been explored (D. Heredia, J. Natera, M. gervaldo, L. Otero, F. Fungo, C.-Y. Lin, K.-T. Wong, *Org. Lett.* 2010, 12, 12; H.-C. Ting, C.-H. Tsai, J.-H. Chen, L.-Y. Lin, S.-H. Chou, K.-T. Wong, T.-W. Huang, C.-C. Wu, *Org. Lett.* 2012, 14, 6338; G. Pozzi, S. Orlandi, M. Cavazzini, D. Minudri, L. Macor, L. Otero, F. Fungo, *Org. Lett.* 2013, 15, 4642; Q. Yan, Y. Zhou, Y.-Q. Zheng, J. Pei, D. Zhao, *Chem. Sci.* 2013, DOI: 10.1039/c3sc5184h). The sterically bulky spiro core can effectively reduce the intermolecular interactions and suppress aggregation-induced self-quenching between the molecules. Meanwhile, an efficient alternating copolymer has been synthesized by incorporating a spirobifluorene core with a benzothiadiazole unit (M. Wang, C. Li, A. Lv, Z. Wang, Z. Bo, *Macromolecules* 2012, 45, 3017). Such copolymer exhibited high hole mobility of up to $7 \times 10^{-3}$ cm$^2$ V$^{-1}$ s$^{-1}$, and a high PCE of up to 4.6% has been achieved for devices based on the copolymer/fullerene blend. While spirobifluorene is a useful building block for designing efficient donor materials, there is scarcely any literature report on utilizing the heterocyclic spiro compounds in the fabrication of OPV devices.

BRIEF SUMMARY OF THE INVENTION

The subject invention provides compositions of and methods of using carbo- and heterocyclic spiro compounds as donor materials for organic photovoltaic (OPV) devices. In preferred embodiments, spiro compounds comprising triarylamine and derivatives thereof demonstrate effective hole-transporting properties in OPV devices, achieving up to 5.46% of PCE.

Advantageously, preferred compounds provided herein are thermally stable and volatile enough to form thin films for the photoactive layer of an OPV device by vacuum deposition or by spin-coating.

In one aspect, the subject invention provides an OPV donor compound of the following Formula:

(I)

wherein A, B, C and D are the same or different and independently selected from optionally substituted arenes, and optionally substituted heteroarenes;

wherein $M^1$ and $M^2$ are independently carbon atoms;

wherein X is optionally present, and if present, X is a carbon atom or a heteroatom, each being optionally substituted with at least one functional group R or being optionally oxidized, wherein the heteroatom is selected from boron, sulfur, oxygen, nitrogen, phosphorus, silicon, germanium, selenium, and tellurium, and R is selected from alkyl, aryl, heteroaryl, and alkoxy groups; and if X is absent, then $M^1$ and $M^2$ are bonded directly to each other; and wherein $D^1$, $D^2$, $D^3$, and $D^4$ are the same or different and independently selected from alkyl, aryl, heteroaryl, alkoxy, and arylalkoxy groups, each being optionally substituted.

Preferred embodiments provide that A, B, C, and D are 5- or 6-membered rings selected from benzenes, pyridines, thiophenes, furans, fused-thiophenes, pyrazoles, pyrimidines, pyrroles, selenophenes, tellurophenes, benzimidazoles, benzofurans, benzothiazoles, benzoxazoles, benzophospholes, indoles, indanes, naphthalenes, anthracenes, pyrenes, thiazoles, pyrans, thiapyrans, carbazoles, dibenzothiophenes, dibenzofurans, dibenzosiloles, fluorenes, and dibenzophospholes, each being optionally substituted.

In certain embodiments, X is optionally absent such that when X is absent, $M^1$ and $M^2$ are bonded to each other directly.

In preferred embodiments, the spiro compound comprises one or more of $D^1$, $D^2$, $D^3$, and $D^4$, each of which is selected from optionally substituted functional groups of alkylaminos, arylamines, thiophenes, oligo-thiophenes, fused-thiophenes, fluorenes, dibenzothiophenes, dibenzofurans, and dibenzophospholes.

In another aspect, the subject invention provides an OPV device comprising, in sequence, an anode, an optional anodic buffer layer, a photoactive layer, an optional exciton-blocking layer, and a cathode, the photoactive layer comprising a fullerene compound, or a derivative thereof, and the carbo- or heterocyclic compound provided herein.

In some embodiments, the carbo- or heterocyclic compound is thermally evaporated in vacuum or spin-coated onto the anodic buffer layer. In a specific embodiment, the carbo- or heterocyclic spiro compound is thermally co-evaporated with the fullerene compound onto the anodic buffered layer.

Advantageously, with PCE reaching about 5.46%, the doping of preferred spiro donor compounds in an acceptor matrix can effectively improve the photovoltaic responses of OPV devices.

Objects, features, and advantages of the invention will be apparent to those skilled in the art from the detailed description of the invention which will now follow, taken in conjunction with the tables, drawings, and the accompanying claims.

DETAILED DISCLOSURE OF THE INVENTION

In the following detailed description, reference is made to the accompanying drawings, depicting exemplary, non-limiting and non-exhaustive embodiments of the invention. These embodiments are described in sufficient detail to enable those having skill in the art to practice the invention, and it is understood that other embodiments may be used, and other changes may be made, without departing from the spirit or scope of the invention. The following detailed description is, therefore, not to be taken in a limiting sense, and the scope of the invention is defined only by the appended claims. All patents, patent applications, provisional applications, and publications referred to or cited herein are incorporated by reference in their entirety, including all figures and tables, to the extent they are not inconsistent with the explicit teachings of this specification.

The subject invention provides compositions of and methods of using carbo- and heterocyclic spiro compounds as donor materials for OPV devices. In preferred embodiments, spiro compounds comprising triarylamine and derivatives thereof demonstrate effective hole-transporting properties in OPV devices, achieving up to 5.46% of PCE.

Advantageously, preferred compounds provided herein are thermally stable and volatile enough to form thin films with an acceptor material by vacuum deposition or by spin-coating.

In one aspect, the subject invention provides an OPV donor compound of the following Formula:

(I)

wherein A, B, C and D are the same or different and independently selected from optionally substituted arenes, and optionally substituted heteroarenes;

wherein $M^1$ and $M^2$ are independently carbon atoms;

wherein X is optionally present, and if present, X is a carbon atom or a heteroatom, each being optionally substituted with at least one functional group R or being optionally oxidized, wherein the heteroatom is selected from boron, sulfur, oxygen, nitrogen, phosphorus, silicon, germanium, selenium, and tellurium, and R is selected from alkyl, aryl, heteroaryl, and alkoxy groups; and if X is absent, then $M^1$ and $M^2$ are bonded directly to each other; and wherein $D^1$, $D^2$, $D^3$, and $D^4$ are the same or different and independently selected from alkyl, aryl, heteroaryl, alkoxy, and arylalkoxy groups, each being optionally substituted.

Preferred embodiments provide that A, B, C, and D are 5- or 6-membered rings selected from benzenes, pyridines, thiophenes, furans, fused-thiophenes, pyrazoles, pyrimidines, pyrroles, selenophenes, tellurophenes, benzimidazoles, benzofurans, benzothiazoles, benzoxazoles, benzophospholes, indoles, indanes, naphthalenes, anthracenes, pyrenes, thiazoles, pyrans, thiapyrans, carbazoles, dibenzothiophenes, dibenzofurans, dibenzosiloles, fluorenes, and dibenzophospholes, each being optionally substituted.

In some embodiments, X comprises at least one substituent R selected from alkyl, aryl, heteroaryl, alkoxy, and arylalkoxy groups, each of which being optionally substituted. Non-limiting examples of R include thiophenes, oligo-thiophenes, and fused-thiophenes.

In certain embodiments, X is optionally absent such that when X is absent, $M^1$ and $M^2$ are bonded to each other directly.

In preferred embodiments, the spiro compound comprises one or more of $D^1$, $D^2$, $D^3$, and $D^4$, each of which is selected from optionally substituted functional groups of alkylaminos, arylamines, thiophenes, oligo-thiophenes, fused-thiophenes, fluorenes, dibenzothiophenes, dibenzofurans, and dibenzophospholes.

In a particularly preferred embodiment, at least one of $D^1$, $D^2$, $D^3$, and $D^4$ is an optionally substituted triarylamine group.

In another aspect, the subject invention provides an OPV device comprising, in sequence, an anode, an anodic buffer layer, a photoactive layer, an exciton-blocking layer, and a cathode, the photoactive layer comprising a fullerene compound, or a derivative thereof, and the carbo- or heterocyclic compound provided herein.

In some embodiments, the carbo- or heterocyclic compound is thermally evaporated in vacuum or spin-coated onto the anodic buffer layer. In a specific embodiment, the carbo- or heterocyclic spiro compound is thermally co-evaporated with the fullerene compound onto the anodic buffered layer.

Advantageously, with PCE reaching about 5.46%, the doping of preferred spiro donor compounds in an acceptor matrix can effectively improve the photovoltaic responses of OPV devices.

The term "optional" or "optionally" means that the subsequently described event or circumstance may or may not occur, and that the description includes instances where said event or circumstance occurs and instances in which it does not. For example, "optionally substituted alkyl" refers to both "alkyl" and "substituted alkyl".

The term "alkyl" as used herein, either alone or in combination, refers to the functional group of a straight or branched hydrocarbon chain that is fully saturated. Preferred alkyl groups are those comprising 1 to 18 carbon atoms, with non-limiting examples including methyl, ethyl, propyl, isopropyl, butyl, isobutyl, tert-butyl, and the like.

The term "alkoxy" as used herein, either alone or in combination, refers to the functional group of a straight or branched alkyl attached to the parent structure through an oxygen atom. Preferred alkoxy groups are those comprising one to eighteen carbon atoms, with non-limiting examples including methoxy, ethoxy, propoxy, isopropoxy, and the like.

The term "aryl" as used herein refers to the functional group of a ring or ring system having a hydrocarbon conjugated π electron system. The term includes monocyclic or fused-ring polycyclic (i.e., rings which share adjacent pairs of atoms) groups provided that the entire ring system is aromatic. Preferred aryl groups provided herein are 5- or 6-membered rings, a non-limiting example being a benzene group.

The term "heteroaryl" as used herein, either alone or in combination, refers to the functional group of an aromatic ring or ring system (i.e., two or more fused rings that share two adjacent atoms) that comprise(s) one or more heteroatoms, that is, an element other than carbon, including but not limited to, nitrogen, oxygen and sulfur, in the ring backbone. The system may comprise at least one ring where the rings may be attached in a pendant manner or may be fused. The heteroaryl group may have 5-18 ring members (i.e., the number of atoms making up the ring backbone, including carbon atoms and heteroatoms), although the present definition also covers the occurrence of the term "heteroaryl" where no numerical range is designated. Preferred heteroaryl groups provided herein comprise 5- or 6-membered rings. Examples of heteroaryl groups include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, benzothienyl, thiophenyl, fused-thiophenyl, selenophenyl, tellurophenyl, benzofuryl, benzophospholyl, pyranyl, thiapyryl, carbazolyl, dibenzothiophenyl, dibenzofuryl, dibenzosilolyl, and dibenzophospholyl.

The term "arylalkoxy" as used herein, either alone or in combination, refers to an aryl group attached to the parent structure through an oxygen atom. Preferred arylalkoxy groups comprise 3 to 7 carbon atoms, with a non-limiting example including phenoxyl.

The term "substituted" refers to an exchange of one or more hydrogen atoms for another atom or group in an unsubstituted parent group. Unless otherwise indicated, when a group is deemed to be "substituted," it is meant that the group is substituted with one or more substituents. "Substituted" may refer to any level of substitution, although mono-, di- and tri-substitutions are preferred. Preferred substituents include halogen, aryl, alkyl, heteroaryl, alkoxy and arylalkoxy.

The term "fullerenes" as used herein, either alone or in combination, refers to $C_{60}$, $C_{70}$, and similar compounds with higher numbers of carbon atoms that can be used as acceptor materials in OPV devices. Exemplary embodiments of fullerene derivatives include phenyl-$C_{61}$-butyric acid methyl ester ($PC_{61}BM$) and phenyl-$C_{71}$-butyric acid methyl ester ($PC_{71}BM$).

Following are examples that illustrate procedures for practicing the invention. These examples should not be construed as limiting. All percentages are by weight and all solvent mixture proportions are by volume unless otherwise noted.

Example 1

Synthesis and Characterization of Heterocyclic Spiro Compounds

Compounds 1-10 were synthesized using the standard Suzuki coupling reaction of mono/dibromo-spiro backbone with the corresponding boronic acid of the pendant D group(s). Exemplary procedures are as follows. $Pd(PPh_3)_4$ was added to a mixture of 4-(N,N-diphenylamino)phenyl-boronic acid and 2,7-dibromospiro-fluorene-9,9'-xanthene in dry THF and aqueous $K_2CO_3$ (2 M). The reaction mixture was heated to reflux overnight under nitrogen. The reaction mixture was then extracted with dichloromethane for at least three times. The organic layer was washed with deionized water several times and was dried over anhydrous $MgSO_4$ and filtered. The solvent was evaporated under vacuum. The crude product was purified by column chromatography over silica using dichloromethane-hexane as the eluent. Further purification was achieved by recrystallization with chloroform-hexane.

Compounds 11 and 12 were synthesized according to the following methodology. 2-Bromobiphenyl was lithiated and reacted with 9H-fluorenone, followed by ring-closing reaction with a catalytic amount of triflic acid. To demonstrate the methodology by example, 2-(2-bromophenyl)benzo[b]thiophene was lithiated by n-butyllithium in dry THF and allowed to react with 9H-fluorenone. The reaction mixture was quenched with deionized water. The reaction mixture was then extracted with dichloromethane for at least three times. The organic layer was washed with deionized water several times and was dried over anhydrous $MgSO_4$ and filtered. The solvent was evaporated under vacuum. The crude product was washed with hexane and the tertiary alcohol intermediate was used without further purification. The tertiary alcohol intermediate was then dissolved in dichloromethane and a catalytic amount of triflic acid was added. The reaction was monitored using TLC analysis until no starting material could be detected. The reaction was washed with deionized water several times and was dried over anhydrous $MgSO_4$ and filtered. The solvent was evaporated under vacuum. The crude product was purified by column chromatography using hexane as the eluent. Further purification was achieved by recrystallization of the product from dichloromethane-methanol.

R = $R_1$; X = NPh (3)
R = $R_1$; X = S (4)
R = $R_1$; X = $SO_2$ (5)
R = $R_2$; X = $SO_2$ (6)
R = $R_3$; X = $SO_2$ (7)

The characteristic spectroscopic properties of compounds 1-12 are as follows.

Compound 1

Yield: 68%. $^1$H NMR (400 MHz, CDCl$_3$, 298 K, relative to Me$_4$Si): δ 6.51 (d, 2H, 8.0 Hz), 6.79 (t, 2H, 6.4 Hz), 6.99-7.09 (m, 16H), 7.17-7.25 (m, 12H), 7.36-7.39 (m, 6H), 7.60 (d, 2H, 8.0 Hz), 7.83 (d, 2H, 8.0 Hz). HRMS (Positive EI) calcd. for C$_{61}$H$_{42}$ON$_2$: m/z=818.3292. found: 818.3279 [M]$^1$.

Compound 2

Yield: 65%. $^1$H NMR (400 MHz, CDCl$_3$, 298 K, relative to Me$_4$Si): δ 6.60 (d, 2H, 2.0 Hz), 6.96-7.06 (m, 16H), 7.10 (d, 4H, 8.0 Hz), 7.21-7.25 (m, 12H), 7.30 (d, 2H, 8.0 Hz), 7.34-7.41 (m, 4H), 7.79 (d, 2H, 8.0 Hz). HRMS (Positive EI) calcd. for C$_{61}$H$_{42}$ON$_2$: m/z=818.3292. found: 818.3271 [M]$^+$.

Compound 3

Yield: 76%. $^1$H NMR (400 MHz, CD$_2$Cl$_2$, 298 K, relative to Me$_4$Si): δ 6.35 (d, 2H, 8.0 Hz), 6.47 (d, 2H, 8.0 Hz), 6.57 (t, 2H, 8.0 Hz), 6.91 (t, 2H, 8.0 Hz), 7.00-7.07 (m, 16H), 7.21-7.26 (m, 8H), 7.43-7.49 (m, 6H), 7.58 (t, 1H, 8.0 Hz), 7.64 (m, 4H), 7.68 (t, 2H, 8.0 Hz), 7.86 (d, 2H, 8.5 Hz). MS (Positive FAB) calcd. for C$_6$H$_{47}$N$_3$: m/z=894.1. found: 894.4 [M]$^+$.

Compound 4

Yield: 70%. $^1$H NMR (400 MHz, CD$_2$Cl$_2$, 298 K, relative to Me$_4$Si): δ 6.63 (d, 2H, 8.0 Hz), 6.89 (t, 2H, 8.0 Hz), 6.99-7.06 (m, 16H), 7.15 (t, 2H, 8.0 Hz), 7.23 (t, 8H, 7.4 Hz), 7.40-7.43 (m, 6H), 7.64 (d, 2H, 8.0 Hz), 7.78 (s, 2H), 7.84 (d, 2H, 8.0 Hz). HRMS (Positive EI) calcd. for C$_{61}$H$_{42}$SN$_2$: m/z=834.3063. found: 834.3063 [M]$^+$.

Compound 5

Yield: 68%. $^1$H NMR (400 MHz, CDCl$_3$, 298 K, relative to Me$_4$Si): δ 6.71 (d, 2H, 8.0 Hz), 6.99-7.08 (m, 16H), 7.23 (t, 8H, 7.5 Hz), 7.28 (d, 2H, 8.0 Hz), 7.37 (d, 4H, 8.0 Hz), 7.46 (t, 2H, 8.0 Hz), 7.60 (s, 2H), 7.67 (d, 2H, 8.0 Hz), 7.87

(d, 2H, 8.0 Hz), 8.24 (d, 2H, 8.0 Hz). MS (Positive FAB) calcd. for $C_{61}H_{42}O_2N_2S$: m/z=867.1. found: 867.3 [M]$^+$.

Compound 6

Yield: 75%. $^1$H NMR (400 MHz, CDCl$_3$, 298 K, relative to Me$_4$Si): δ 6.80 (d, 2H, 8.0 Hz), 7.27-7.30 (m, 4H), 7.37-7.43 (m, 10H), 7.52-7.59 (m, 6H), 7.75-7.79 (m, 6H), 7.84 (d, 2H, 8.0 Hz), 8.02 (d, 2H, 8.0 Hz), 8.13 (d, 4H, 8.0 Hz), 8.32 (d, 2H, 8.0 Hz). MS (Positive FAB) calcd. for $C_{61}H_{38}O_2N_2S$: m/z=863.0. found: 863.3 [M]$^+$.

Compound 7

Yield: 75%. $^1$H NMR (400 MHz, CDCl$_3$, 298 K, relative to Me$_4$Si): δ 1.46 (s, 36H) 6.79 (d, 2H, 8.0 Hz), 7.37-7.43 (m, 10H), 7.52-7.59 (m, 6H), 7.75-7.79 (m, 6H), 7.84 (d, 2H, 8.0 Hz), 8.01 (d, 2H, 8.0 Hz), 8.12 (s, 4H), 8.31 (d, 2H, 8.0 Hz). MS (Positive FAB) calcd. for $C_{77}H_{70}O_2N_2S$: m/z=1087.5. found: 1086.1 [M−1]$^+$.

Compound 8

Yield: 78%. $^1$H NMR (400 MHz, CDCl$_3$, 298 K, relative to Me$_4$Si): δ 6.81 (d, 2H, 8.0 Hz), 6.89 (s, 2H), 6.98-7.06 (m, 16H), 7.11 (t, 2H, 8.0 Hz), 7.19-7.25 (m, 8H), 7.26-7.31 (m, 4H), 7.37 (t, 2H, 8.0 Hz), 7.58 (d, 2H, 8.0 Hz), 7.84 (d, 2H, 8.0 Hz), 7.88 (d, 2H, 8.0 Hz). HRMS (Positive EI) calcd. for $C_{61}H_{42}N_2$: m/z=802.3343. found: 802.3356 [M]$^+$.

Compound 9

Yield: 78%. $^1$H NMR (400 MHz, CDCl$_3$, 298 K, relative to Me$_4$Si): δ 1.20 (s, 18H), 6.81 (s, 2H), 7.07 (s, 2H), 7.26-7.29 (m, 4H), 7.38-7.45 (m, 10H), 7.53 (d, 4H, 8.3 Hz), 7.68 (d, 4H, 8.3 Hz), 7.76-7.78 (m, 4H), 8.03 (d, 2H, 7.8 Hz), 8.13 (d, 4H, 7.8 Hz).

Compound 10

Yield: 73%. $^1$H NMR (400 MHz, CD$_2$Cl$_2$, 298 K, relative to Me$_4$Si): δ 6.55 (d, 1H, 7.5 Hz), 6.61 (s, 1H), 6.80 (d, 2H, 7.5 Hz), 6.95-7.08 (m, 9H), 7.13 (t, 2H, 7.6 Hz), 7.22 (t, 4H, 7.5 Hz), 7.30 (t, 1H, 4.3 Hz), 7.37 (t, 4H, 7.5 Hz), 7.52 (d, 1H, 7.6 Hz), 7.84 (d, 2H, 7.6 Hz). HRMS (Positive EI) calcd. for $C_{41}H_{27}NS$: m/z=565.1859. found: 565.1858 [M]$^+$.

Compound 11

Yield: 56%. $^1$H NMR (400 MHz, Acetone-d$_6$, 298 K, relative to Me$_4$Si): δ 6.52 (d, 1H, 7.6 Hz), 6.70 (d, 1H, 7.6 Hz), 6.74 (d, 2H, 7.6 Hz), 7.02 (t, 1H, 8.0 Hz), 7.15 (t, 3H, 7.6 Hz), 7.21 (t, 1H, 8.0 Hz), 7.39-7.47 (m, 3H), 7.75 (d, 1H, 8.0 Hz), 7.97 (d, 1H, 7.6 Hz), 8.08 (d, 2H, 7.6 Hz). HRMS (Positive EI) calcd. for $C_{27}H_{16}S$: m/z=372.0967. found: 372.0226 [M]$^+$.

Compound 12

Yield: 65%. $^1$H NMR (400 MHz, Acetone-d$_6$, 298 K, relative to Me$_4$Si): δ 1.58 (s, 6H), 6.64 (d, 1H, 7.6 Hz), 6.71 (d, 2H, 7.6 Hz), 7.09-7.25 (m, 6H), 7.40-7.44 (m, 3H), 7.50 (d, 1H, 7.3 Hz), 7.56 (d, 1H, 7.3 Hz), 8.03 (t, 3H, 7.6 Hz), 8.20 (s, 1H). HRMS (Positive EI) calcd. for $C_{34}H_{24}$: M/Z=432.1873. found: 432.1861 [M]$^+$.

Example 2

UV-Vis Absorption Properties of the Spiro Compounds

All the carbo- and heterocyclic spiro compounds showed intense absorption band at ca. 350-450 nm which was attributed to the π-π* absorption. FIGS. 2-7 show the UV-vis absorption and emission spectra of compounds 1-7 in dichloromethane at 298 K and the photophysical properties of all compounds are shown in Table 1. When the heterocyclic spiro core had been changed to a carbocyclic spiro core, compounds 1, 3, 4 and 5 showed red-shifted absorption bands, as compared to that of compound 8 without any heteroatom on the spiro backbone. The substitution of the donor moiety with a less electron-rich carbazole moiety (i.e. compounds 6 and 7) led to a blue-shifted UV absorption spectrum (i.e. compound 5). Compound 10 with an electron-rich thiophene ring embedded in the spiro core showed the most red-shifted absorption band, which was in good agreement with the electrochemical data.

TABLE 1

Photophysical data of compounds 1-12.

| Compound | Medium (T [K]) | Absorption $\lambda_{max}$ [nm], $\epsilon_{max}$ [dm$^3$mol$^{-1}$cm$^{-1}$] | Emission $\lambda_{max}$ [nm] |
|---|---|---|---|
| 1 | CH$_2$Cl$_2$ (298) | 372 (78830), 302 (40550) | 456 |
| 2 | CH$_2$Cl$_2$ (298) | 345 (65520), 309 (59440) | 419 |
| 3 | CH$_2$Cl$_2$ (298) | 372 (74180), 301 (44480) | 451 |
| 4 | CH$_2$Cl$_2$ (298) | 375 (75930), 298 (42320) | 453 |
| 5 | CH$_2$Cl$_2$ (298) | 380 (87320), 300 (43410) | 460 |
| 6 | CH$_2$Cl$_2$ (298) | 346 (88140), 294 (54540) | 427 |
| 7 | CH$_2$Cl$_2$ (298) | 353 (79200), 298 (58040) | 449 |
| 8 | CH$_2$Cl$_2$ (298) | 370 (76590), 309 (40810) | 452 |
| 9 | CH$_2$Cl$_2$ (298) | 345 (63880), 316 (41620), 294 (50550) | 417 |
| 10 | CH$_2$Cl$_2$ (298) | 402 (32220), 380 (43750), 305 (20050) | 458 |
| 11 | CH$_2$Cl$_2$ (298) | 337 (19890), 322 (25370) | 402 |
| 12 | CH$_2$Cl$_2$ (298) | 343 (48920), 335 (25190), 327 (25000), 310 (31040) | 366, 389, 408 |

Example 3

Electrochemical Properties of the Spiro Compounds

To probe the electrochemical properties, cyclic voltammetry was carried out in a three-electrode cell with 0.1 M $^n$Bu$_4$NPF$_6$ as the supporting electrolyte in dimethylformamide for compounds 1 to 12, except that compound 9 was carried out in tetrahydrofuran. The ferrocenium/ferrocene couple (Fc$^+$/Fc) was used as the internal reference.

Figure 1:
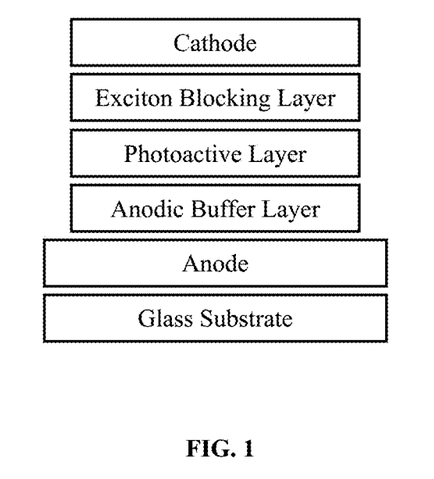
FIG. 1 shows a preferred structure of an OPV device wherein the photoactive layer comprises a carbo- and heterocyclic spiro compound in combination with a fullerene compound as the acceptor material.
Figure 2:
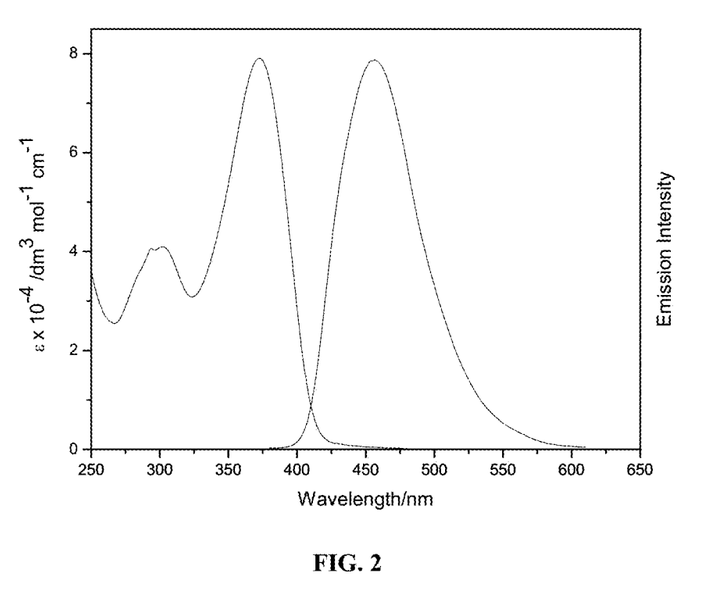
FIG. 2 shows the UV-vis absorption and emission spectra of compound 1 in dichloromethane at 298 K. No instrumental correction was applied for the emission wavelength.
Figure 3:
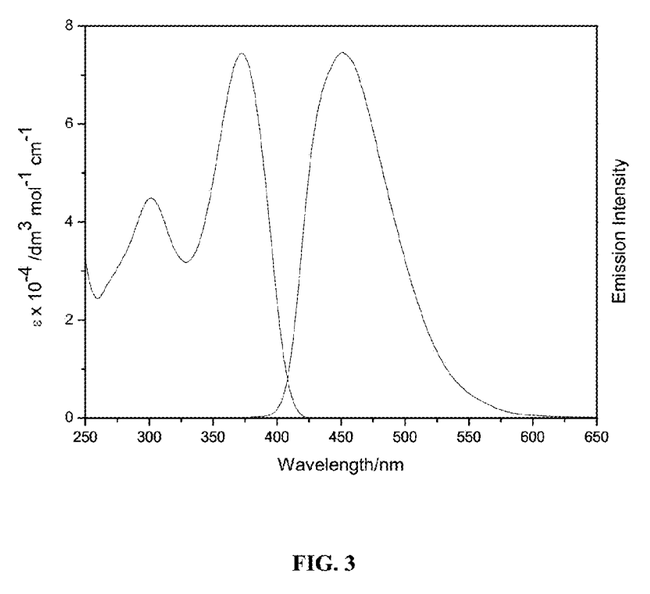
FIG. 3 shows the UV-vis absorption and emission spectra of compound 3 in dichloromethane at 298 K. No instrumental correction was applied for the emission wavelength.
Figure 4:
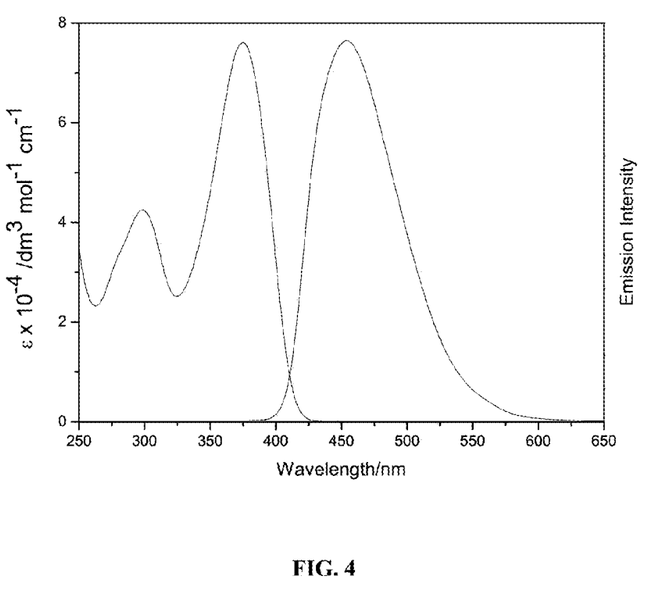
FIG. 4 shows the UV-vis absorption and emission spectra of compound 4 in dichloromethane at 298 K. No instrumental correction was applied for the emission wavelength.
Figure 5:
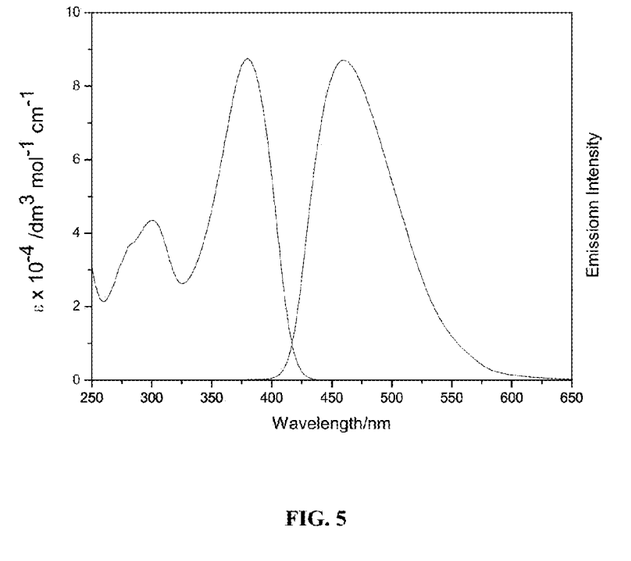
FIG. 5 shows the UV-vis absorption and emission spectra of compound 5 in dichloromethane at 298 K. No instrumental correction was applied for the emission wavelength.
Figure 6:
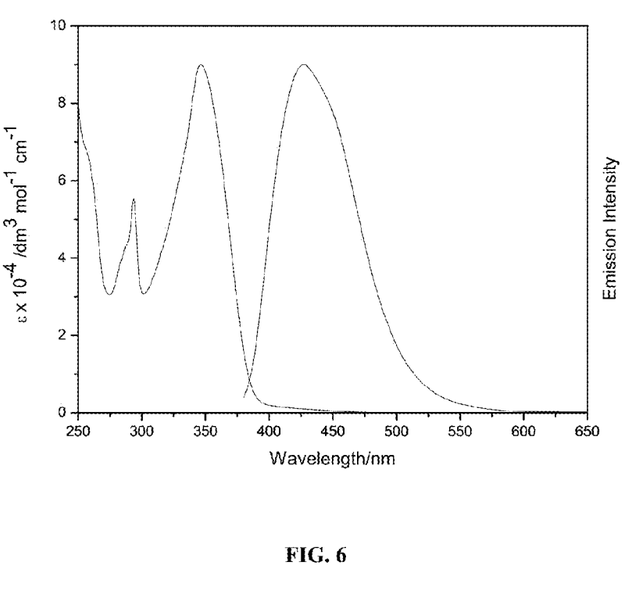
FIG. 6 shows the UV-vis absorption and emission spectra of compound 6 in dichloromethane at 298 K. No instrumental correction was applied for the emission wavelength.
Figure 7:
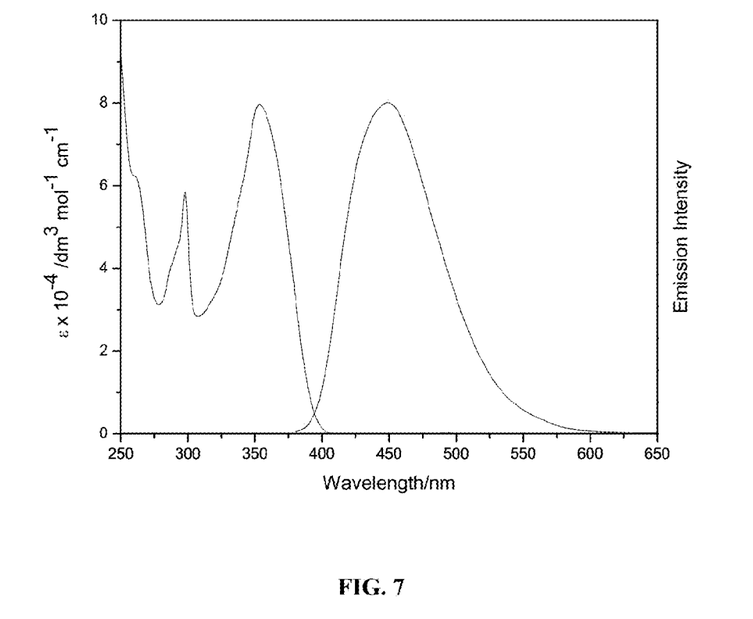
FIG. 7 shows the UV-vis absorption and emission spectra of compound 7 in dichloromethane at 298 K. No instrumental correction was applied for the emission wavelength.
Figure 8:
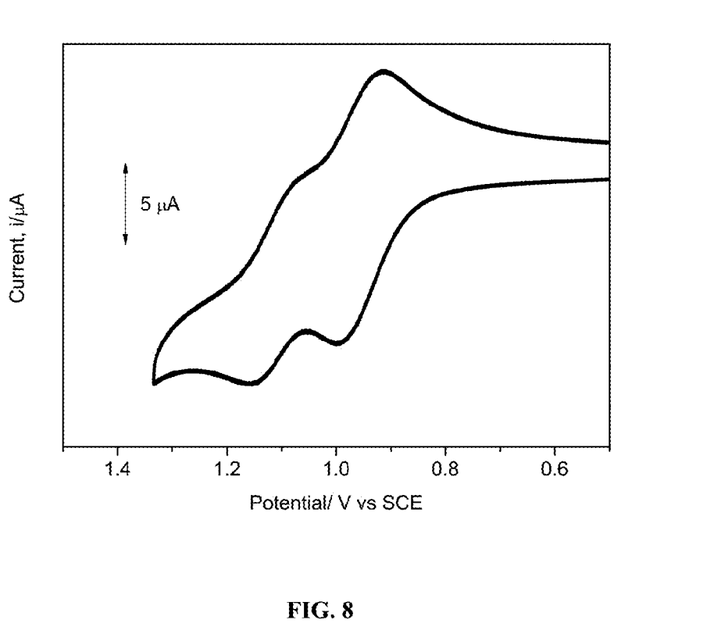
FIG. 8 shows the cyclic voltammogram of compound 3 in a three-electrode cell with 0.1 M $^n$Bu$_4$NPF$_6$ as the supporting electrolyte in dimethylformamide.
Figure 9:
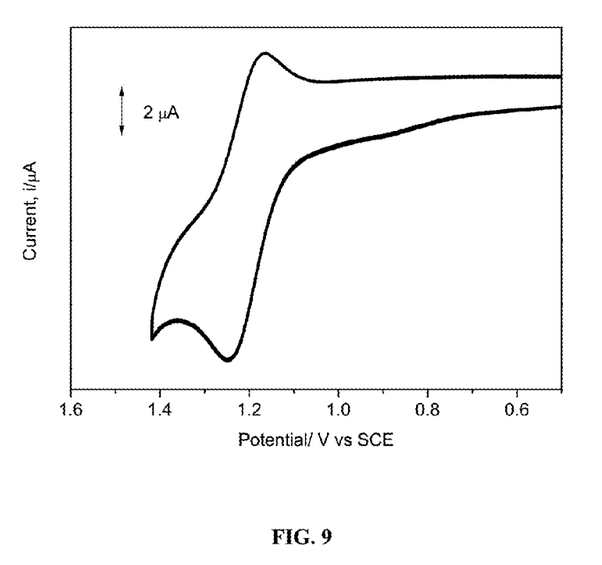
FIG. 9 shows the cyclic voltammogram of compound 7 in a three-electrode cell with 0.1 M $^n$Bu$_4$NPF$_6$ as the supporting electrolyte in dimethylformamide.
Figure 10:
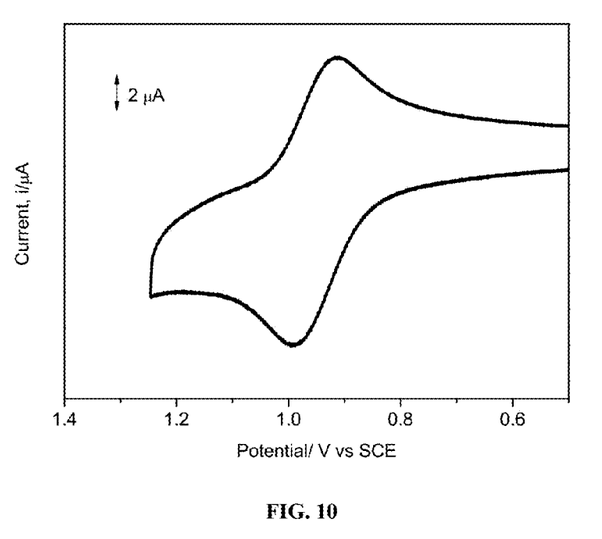
FIG. 10 shows the cyclic voltammogram of compound 8 in a three-electrode cell with 0.1 M $^n$Bu$_4$NPF$_6$ as the supporting electrolyte in dimethylformamide.

The potentials for oxidation of spiro compounds with heteroatoms (compounds 1-7) were more positive as compared with that of spiro compound without heteroatom (compound 8). The substitution of triphenylamine moiety (i.e. compounds 1-5, and 8) with less electron-rich carbazole moiety (i.e. compounds 6 and 7) shifted the oxidation couples to more positive values. The potential of oxidation for compound 10 was the least negative among the series. Compound 3, which comprises nitrogen atom as the heteroatom of the spiro backbone, showed two quasi-reversible oxidation couples (FIG. 8), and no oxidation wave was found in compound 12 within the solvent window of dimethylformamide. Compounds 9 and 12 each displayed a single reduction couple; while other compounds showed multiple reduction couples that were attributed to the electron reductions of the spiro cores. FIGS. 9 and 10 are the cyclic voltammograms of compounds 7 and 8 in dimethylformamide. The electrochemical data is summarized in Table 2.

TABLE 2

Electrochemical properties of compounds 1-12.

| Compound | Oxidation $E_{1/2}$/V$^b$ vs SCE [$E_{pa}$/V$^b$ vs SCE] ($\Delta E_p$/mV) | Reduction $E_{1/2}$/V$^b$ vs SCE [$E_{pc}$/V$^b$ vs SCE] ($\Delta E_p$/mV) |
|---|---|---|
| 1 | +0.95 (81) | −2.13 (76) [−2.44]$^d$ [−2.82]$^d$ |
| 2 | +0.96 (80) | [−2.64]$^d$ [−2.78]$^d$ |

TABLE 2-continued

Electrochemical properties of compounds 1-12.

| Compound | Oxidation $E_{1/2}/V^b$ vs SCE $[E_{pa}/V^b$ vs SCE] $(\Delta E_p/\text{mV})$ | Reduction $E_{1/2}/V^b$ vs SCE $[E_{pc}/V^b$ vs SCE] $(\Delta E_p/\text{mV})$ |
|---|---|---|
| 3 | +0.95 (83) | −2.16 (83) |
|   | +1.10 (87) | [−2.47]$^d$ |
|   |   | [−2.75]$^d$ |
|   |   | [−3.04]$^d$ |
| 4 | +0.96 (80) | −2.11 (82) |
|   |   | [−2.42]$^d$ |
|   |   | [−2.73]$^d$ |
| 5 | +0.96 (80) | −2.05 (83) |
|   |   | [−2.37]$^d$ |
| 6 | [+1.35]$^c$ | −1.97 (66) |
|   |   | [−2.31]$^d$ |
| 7 | +1.20 (82) | −1.99 (63) |
|   |   | [−2.32]$^d$ |
|   |   | [−2.61]$^d$ |
| 8 | +0.94 (85) | −2.15 (86) |
|   |   | −2.39 (88) |
| 9$^e$ | [+1.57]$^c$ | [−2.38]$^d$ |
| 10 | +0.84 (65) | −2.11 (63) |
|   | [+1.07]$^c$ | [−2.54]$^d$ |
|   |   | [−2.71]$^d$ |
| 11 | [+1.46]$^c$ | −2.30 (83) |
|   |   | [−2.66]$^d$ |
|   |   | [−2.72]$^d$ |
| 12 | — | [−2.37]$^d$ |

$^a$0.1M $^n$Bu$_4$NPF$_6$ (TBAH) as supporting electrolyte at room temperature; scan rate 100 mV s$^{-1}$.
$^b$E$_{1/2}$ = (E$_{pa}$ + E$_{pc}$)/2; E$_{pa}$ and E$_{pc}$ are peak anodic and peak cathodic potentials, respectively.
$^c$Anodic peak potential for the irreversible oxidation wave.
$^d$Cathodic peak potential for the irreversible reduction wave.
$^e$THF was used as solvent.

Example 4

Fabrication and Photovoltaic Responses of OPV Devices

An OPV device according to a preferred embodiment of the invention was constructed in the following manner:
(a) A transparent anode indium-tin-oxide (ITO)-coated borosilicate glass substrate with sheet resistance of 15 ohm square$^{-1}$ was ultrasonicated in the commercial detergent Decon 90, rinsed in deionized water having a resistivity of 18.2 MΩ for 15 minutes, and then dried in an oven at 120 degree C. for an hour. The substrate was then subjected to an UV-ozone treatment in a Jelight 42-220 UVO-Cleaner equipped with a mercury grid lamp for 15 minutes in order to remove any residual water;
(b) The substrate was put into a vacuum chamber, and the chamber was pumped down from 1 bar to 5×10 mbar;
(c) A 2-nm thick molybdenum(VI) oxide (MoO$_3$) anodic buffer layer was deposited by thermal evaporation on the ITO-coated glass substrate;
(d) A 60-nm thick photoactive layer was deposited by thermal evaporation on the MoO$_3$ layer, in which compound 1 as the donor was co-evaporated with C$_{70}$ as the acceptor at different concentrations (i.e. 3, 5, 7, and 9% by weight) to form the photoactive layer;
(e) A 8-nm thick bathophenanthroline (BPhen) exciton blocking layer was deposited by thermal evaporation on the photoactive layer; and
(f) A 100-nm thick aluminum (Al) layer was deposited by thermal evaporation on the BPhen layer to form a cathode.

All organic materials and metal were prepared by thermal evaporation from tantalum boats by applying current through the tantalum boats. Deposition rates were monitored with a quartz oscillation crystal and a Sigma SQM-242 quartz crystal card. The quartz oscillation was controlled at 0.1-0.2 nm s$^{-1}$ for both the organic and metal layers. J-V characteristics of the OPV devices were measured with a programmable Keithley model 2420 power source. The photocurrent was measured under illumination from an Oriel 300 W solar simulator equipped with AM1.5 G (AM: air mass; G: global) filter and the light intensity was measured with an Oriel KG-5 reference cell. For the IPCE measurements, devices were irradiated with monochromatic light of variable wavelength through an Oriel Cornerstone 260 ¼ m monochromator with a 300 W xenon arc lamp (Oriel Model No. 66984) as the light source. The intensity of the source at each wavelength was determined using a calibrated silicon detector (Oriel Model No. 71639). The photocurrent under short-circuit conditions was then recorded for each device at 10 nm intervals using a dual channel radiometer (Oriel Merlin Digital Lock-in Radiometry System Model No. 7104).

Example 5

Photovoltaic Response of a Control OPV Device

A C$_{70}$-only device was fabricated as a control cell, in which the same materials and processing procedures were employed as described in Example 4, except that a pristine C$_{70}$ acceptor was used as the photoactive layer.

Figures 11, 12:
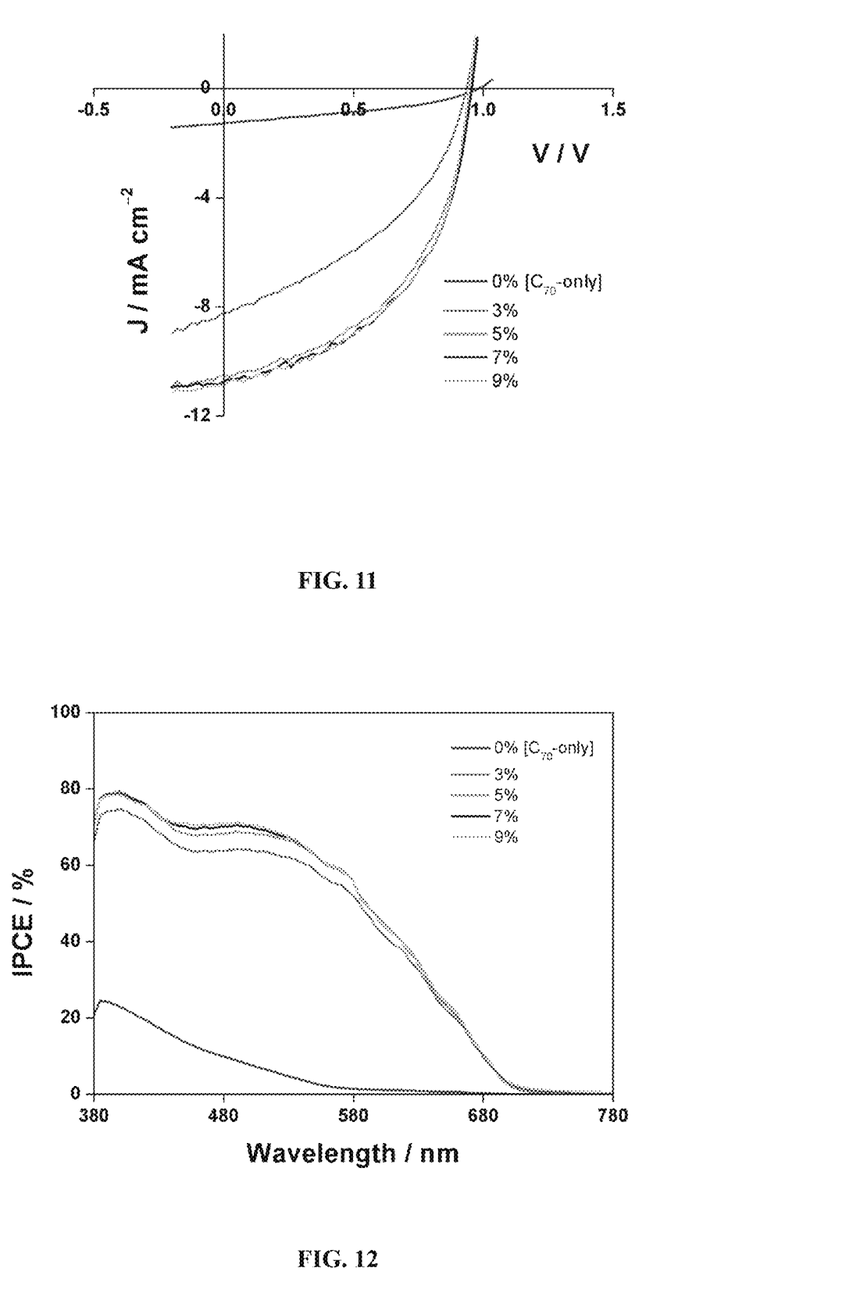
FIG. 11 shows current density-voltage (J-V) curves of devices with compound 1 as the donor doped in $C_{70}$ acceptor at different concentrations.
FIG. 12 shows the incident-photon-to-current efficiency (IPCE) curves of devices with compound 1 as donor doped in $C_{70}$ acceptor at different concentrations.

FIG. 11 shows the J-V curves of devices with compound 1 as donor doped in C$_{70}$ acceptor at different concentrations. Not surprisingly, the C$_{70}$-only cell showed a poor photovoltaic response, with short-circuit density (J$_{SC}$)=1.27 mA cm$^{-2}$; open-circuit voltage (V$_{OC}$)=0.98 V; FF=0.37; PCE=0.46%. With the incorporation of compound 1 as the donor, the photovoltaic responses were dramatically improved. The J$_{SC}$ of OPV devices increased significantly from about 1.27 mA cm$^{-2}$ to about 10.78 mA cm$^{-2}$ when the dopant concentration of compound 1 increased from 0 to about 9%. Meanwhile, the FF of the devices was improved from about 0.37 to about 0.50. Particularly, the optimized device with about 9% of compound 1 demonstrated a high J$_{SC}$ of about 10.78 mA cm$^{-2}$ and a high V$_{OC}$ of about 0.95 V. These values correspond to a high PCE of about 5.1%, much higher than that of the C$_{70}$-only cell (about 0.46%). In addition, the doping of compound 1 could broaden the spectral coverage as well as increase the IPCE of the devices, as depicted in FIG. 12. The plateau sensitivity of the doped devices was found to fully cover the visible spectrum between 380 to 700 nm, which corresponded well to the superposition of the spectral absorption of C$_{70}$ and compound 1. The IPCE of the device doped with about 9% of compound 1 at 490 nm was approximately 70.7%, an order of magnitude higher than that of the C$_{70}$-only device (about 7.8%).

Example 6

Photovoltaic Response of OPV Devices Fabricated with Spiro Compounds as Donor Materials The same materials and processing procedures were employed as described in Example 4, except that compounds 2-8 and 10 were doped in a C$_{70}$ acceptor matrix to form a photoactive layer.

Under 1 sun light illumination, promising photovoltaic responses with J$_{SC}$ ranging from about 3.96 to about 11.00 mA cm$^{-2}$ were obtained when the carbo- or heterocyclic spiro compounds were doped at about 7% (by weight) in the C$_{70}$ acceptor matrix. In addition, the FFs of all devices were improved. These improved photovoltaic responses yielded highly efficient OPV devices with PCEs of up to 5.46%. Table 3 summarizes the photovoltaic responses of as-prepared devices with 7% of compounds 1-8 and 10 as the donor, respectively, doped in a C$_{70}$ acceptor matrix and after thermal annealing at 80° C. for 5 minutes. These results demonstrate that the carbo- and heterocyclic spiro compounds are promising donor materials in the fabrication of efficient small molecular-based OPV devices.

TABLE 3

Photovoltaic response of OPV devices fabricated with different spiro compounds.

| Compound | J$_{SC}$ (mA cm$^{-2}$) | V$_{OC}$ (V) | FF | PCE (%) |
|---|---|---|---|---|
| C$_{70}$-only | 1.27 | 0.98 | 0.37 | 0.46 |
| 1 | 10.68 | 0.95 | 0.50 | 5.07 |
| 2 | 10.87 | 0.98 | 0.41 | 4.37 |
| 3 | 10.60 | 0.94 | 0.50 | 4.98 |
| 4 | 10.78 | 0.94 | 0.49 | 4.97 |
| 5 | 10.95 | 0.94 | 0.53 | 5.46 |
| 6 | 3.96 | 1.07 | 0.27 | 1.14 |
| 7 | 8.70 | 1.16 | 0.36 | 3.63 |
| 8 | 11.00 | 0.93 | 0.52 | 5.32 |
| 10 | 6.95 | 0.87 | 0.44 | 2.66 |

These examples should not be construed as limiting the scope of the invention, but as providing illustrations of some of the embodiments of the invention. It is being understood that changes and variations can be made therein without deviating from the scope and the spirit of the invention as hereinafter claimed.

All patents, patent applications, provisional applications, and publications referred to or cited herein are incorporated by reference in their entirety, including all figures and tables, to the extent they are not inconsistent with the explicit teachings of this specification.

REFERENCES

1. Z. He, C. Zhong, S. Su, M. Xu, H. Wu, Y. Cao, *Nat. Photonics* 2012, 6, 591; J. You, L. Dou, K. Yoshimura, T. Kato, K. Ohya, T. Moriarty, K. Emery, C. Chen, J. Gao, Y. Yang, *Nat. Commun.* 2013, 4, 1446.
2. D. Kearns, M. Calvin, *J. Chem. Phys.* 1958, 29, 950.
3. C. W. Tang, *Appl. Phys. Lett.* 1986, 48, 183.
4. N. S. Sariciftci, D. Braun, C. Zhang, V. I. Srdanov, A. J. Heeger, G. Stucky, F. Wudl, *Appl. Phys. Lett.*, 1993, 62, 585.
5. T. P. I. Saragi, T. Spehr, A. Siebert, T. F. Lieker, J. Salbeck, *Chem. Rev.* 2007, 107, 1011.
6. C. Wu, W. Liu, W. Hung, T. Liu, Y. Lin, H. Lin, K. Wong, Y. Chien, R. Chen, T. Hung, T. Chao, Y. Chen, *Appl. Phys. Lett.* 2005, 87, 052103.
7. D. Heredia, J. Natera, M. gervaldo, L. Otero, F. Fungo, C.-Y. Lin, K.-T. Wong, *Org. Lett.* 2010, 12, 12.
8. H.-C. Ting, C.-H. Tsai, J.-H. Chen, L.-Y. Lin, S.-H. Chou, K.-T. Wong, T.-W. Huang, C.-C. Wu, *Org. Lett.* 2012, 14, 6338.
9. G. Pozzi, S. Orlandi, M. Cavazzini, D. Minudri, L. Macor, L. Otero, F. Fungo, *Org. Lett.* 2013, 15, 4642.
10. Q. Yan, Y. Zhou, Y.-Q. Zheng, J. Pei, D. Zhao, *Chem. Sci.* 2013, DOI: 10.1039/c3sc5184h.
11. M. Wang, C. Li, A. Lv, Z. Wang, Z. Bo, *Macromolecules* 2012, 45, 3017.

We claim:

1. A heterocyclic spiro compound of the following Formula:

(I)

wherein A, B, C, and D are benzenes;
wherein X is a heteroatom or an oxidized heteroatom, each being optionally substituted with at least one functional group R, wherein the heteroatom is sulfur and R is selected from alkyl, aryl, heteroaryl, and alkoxy groups; and
wherein D$^1$ and D$^3$ are absent, and wherein D$^2$ and D$^4$ are present and independently selected from optionally substituted functional groups of alkylaminos, arylamines, thiophenes, oligo-thiophenes, fused-thiophenes, fluorenes, dibenzothiophenes, dibenzofurans, and dibenzophospholes.

2. An organic photovoltaic (OPV) device, comprising in sequence an anode, an anodic buffer layer, a photoactive layer, an exciton-blocking layer, and a cathode, the photoactive layer comprising a fullerene compound, or a derivative thereof, and the heterocyclic spiro-compound according to claim 1.

3. The device according to claim 2, wherein the spiro compound is thermally evaporated or spin-coated onto the anodic buffer layer.

4. The device according to claim 2, wherein the heterocyclic Spiro compound is thermally co-evaporated with the fullerene compound, or a derivative thereof, onto the anodic buffered layer.

* * * * *

UNITED STATES PATENT AND TRADEMARK OFFICE
CERTIFICATE OF CORRECTION

PATENT NO. : 9,691,989 B2
APPLICATION NO. : 14/823520
DATED : June 27, 2017
INVENTOR(S) : Vivian Wing-Wah Yam, Mei-Yee Chan and Chin-Yiu Chan

It is certified that error appears in the above-identified patent and that said Letters Patent is hereby corrected as shown below:

In the Specification

Column 10,

Lines 1-33, "
The characteristic spectroscopic properties of compounds 1-12 are as follows."

should read

Signed and Sealed this
Thirteenth Day of March, 2018

Andrei Iancu
*Director of the United States Patent and Trademark Office*

$R_1 =$ $R_2 =$ $R_3 =$

--

The characteristic spectroscopic properties of compounds 1-12 are as follows.--.
Line 40, "[M]¹" should read --[M]⁺--.
Line 54, "C₆H₄₇N₃" should read --C₆₇H₄₇N₃--.

Column 13,
Line 52, "5×10 mbar;" should read --5×10⁻⁶ mbar;--.